US012566165B2

(12) United States Patent
Yang et al.

(10) Patent No.: US 12,566,165 B2
(45) Date of Patent: Mar. 3, 2026

(54) METHOD AND SYSTEM FOR PREDICTING EFFLUENT AMMONIA NITROGEN (NH₄—N) AND ELECTRONIC DEVICE

(71) Applicant: BEIJING UNIVERSITY OF TECHNOLOGY, Beijing (CN)

(72) Inventors: Cuili Yang, Beijing (CN); Sheng Yang, Beijing (CN); Junfei Qiao, Beijing (CN)

(73) Assignee: Beijing University of Technology, Beijing (CN)

( * ) Notice: Subject to any disclaimer, the term of this patent is extended or adjusted under 35 U.S.C. 154(b) by 475 days.

(21) Appl. No.: 18/334,725

(22) Filed: Jun. 14, 2023

(65) Prior Publication Data

US 2024/0310350 A1     Sep. 19, 2024

(30) Foreign Application Priority Data

Mar. 17, 2023     (CN) .......................... 202310273240.8

(51) Int. Cl.
| | |
|---|---|
| *G01N 33/18* | (2006.01) |
| *C02F 1/00* | (2023.01) |
| *C02F 101/16* | (2006.01) |

(52) U.S. Cl.
CPC .............. *G01N 33/188* (2013.01); *C02F 1/00* (2013.01); *C02F 2101/16* (2013.01)

(58) Field of Classification Search
CPC ...... G01N 33/188; C02F 1/00; C02F 2101/16
See application file for complete search history.

(56) References Cited

U.S. PATENT DOCUMENTS

| | | | | |
|---|---|---|---|---|
| 2020/0225655 | A1* | 7/2020 | Cella | G05B 19/41865 |
| 2022/0058211 | A1* | 2/2022 | Wismüller | G06F 16/2264 |
| 2023/0043793 | A1* | 2/2023 | Shankar | H04L 67/535 |

FOREIGN PATENT DOCUMENTS

| | | | | |
|---|---|---|---|---|
| CN | 105978732 A | * | 9/2016 | H04L 41/145 |
| CN | 110837886 A | * | 2/2020 | G06Q 50/26 |

(Continued)

OTHER PUBLICATIONS

Long, J., Zhang, S., & Li, C. (2020). Evolving Deep Echo State Networks for Intelligent Fault Diagnosis. IEEE Transactions on Industrial Informatics, 16(7), 4928-4937. https://doi.org/10.1109/TII.2019.2938884 (Year: 2020) (Year: 2020).*

(Continued)

*Primary Examiner* — Catherine T. Rastovski
*Assistant Examiner* — Nyla Gavia

(57)     ABSTRACT

The present disclosure provides a method and system for predicting effluent ammonia nitrogen (NH₄—N) and an electronic device. The method includes: obtaining data to be tested; and inputting the data to be tested into a trained deep echo state network, to obtain predicted NH₄—N concentration. A method for establishing the deep echo state network includes: establishing an original network, where the original network includes a plurality of input variables and reservoirs, and a principal component analysis (PCA) mapping layer is added between adjacent ones of the reservoirs; initializing the original network to obtain an initialized network; performing parameter optimization on the initialized network by a matrix generation method of singular value decomposition and a competitive swarm optimizer (CSO) algorithm, to obtain an optimized network; and training and testing the optimized network, to obtain the trained deep echo state network.

20 Claims, 4 Drawing Sheets

(56)  References Cited

FOREIGN PATENT DOCUMENTS

| CN | 111914470 | A | * | 11/2020 | ............. | G06F 30/27 |
| CN | 112614346 | B | * | 2/2022 | ............. | G06N 3/045 |
| CN | 115061203 | A | * | 9/2022 | ............. | G01V 1/288 |

OTHER PUBLICATIONS

Huang, Z., Yang, C., Chen, X., Zhou, X., Chen, G., Huang, T., & Gui, W. (2021). Functional Deep Echo State Network improved by a bi-level optimization approach for multivariate time series classification. Applied Soft Computing, 106, 107314. https://doi.org/10.1016/j.asoc.2021.107314 (Year: 2021) (Year: 2021).*

* cited by examiner

METHOD AND SYSTEM FOR PREDICTING EFFLUENT AMMONIA NITROGEN (NH₄—N) AND ELECTRONIC DEVICE

CROSS REFERENCE TO RELATED APPLICATION

This patent application claims the benefit and priority of Chinese Patent Application No. 2023102732408, filed with the China National Intellectual Property Administration on Mar. 17, 2023, the disclosure of which is incorporated by reference herein in its entirety as part of the present application.

TECHNICAL FIELD

The present disclosure relates to the field of water treatment technologies, and in particular, to a method for predicting effluent ammonia nitrogen (NH₄—N).

BACKGROUND

With the rapid development of urbanization and industrialization, the hydrographic environment has been seriously damaged. Wastewater discharge not only seriously affects our daily life, but also destroys ecological balance of nature. To reduce the discharge of wastewater and recycle water, wastewater treatment plants have been established all over the world. During wastewater treatment, NH₄—N concentration is an important parameter used to measure the performance of a wastewater treatment process (WWTP). Excessive discharge of ammonia nitrogen is a main reason for eutrophication of rivers and black or odor water. To resolve the problem, some laboratory detection methods based on chemistry and biology are widely used. However, these methods have long detection time and are easily affected by environmental factors.

In addition, due to the continuous development of sensors and information technologies, the wastewater treatment plants can record and save a large amount of historical data. Therefore, a data-driven method is widely used for predicting effluent NH₄—N. However, because the wastewater treatment process is a complex system with characteristics of high nonlinearity, large delay, and large time-varying. To sum up, in the conventional technology, prediction of the effluent NH₄—N has problems of low prediction accuracy, weak stability, and high maintenance costs.

SUMMARY

An objective of the present disclosure is to provide a method and system for predicting effluent NH₄—N and an electronic device, to resolve problems of predicting the effluent NH₄—N in a conventional technology, for example, low prediction accuracy, weak stability, and high maintenance costs.

To achieve the above objective, the present disclosure provides the following technical solutions:

A method for predicting effluent NH₄—N includes:

obtaining data to be tested; and inputting the data to be tested into a trained deep echo state network, to obtain predicted NH₄—N concentration, where a method for establishing the deep echo state network includes:

establishing an original network, where the original network includes a plurality of input variables and reservoirs, and a principal component analysis (PCA) mapping layer is added between adjacent ones of the reservoirs;

initializing the original network to obtain an initialized network;

performing parameter optimization on the initialized network by a matrix generation method of singular value decomposition and a competitive swarm optimizer (CSO) algorithm, to obtain an optimized network; and training and testing the optimized network, to obtain the trained deep echo state network.

Preferably, the input variable includes:

a temperature, a redox potential, a dissolved oxygen concentration, content of total suspended solids, a pH value, total effluent phosphorus, and total influent phosphorus.

Preferably, the initializing the original network includes:

setting a parameter of the original network and setting a structure of the original network.

Preferably, the setting a structure of the original network includes:

converting all the input variables into five input nodes by a principal component analysis method; and determining the structure of the original network based on the input nodes and effluent NH₄—N concentration.

Preferably, the setting a parameter of the original network includes:

using a tan h function as an activation function of a neuron, and initializing the parameter of the original network.

Preferably, the performing parameter optimization on the initialized network by a matrix generation method of singular value decomposition and a competitive swarm optimizer (CSO) algorithm, to obtain an optimized network includes:

establishing an input weight matrix and a reservoir weight of the initialized network by the matrix generation method of singular value decomposition;

determining a decision variable based on the input weight matrix, the reservoir weight, and a delay factor of the initialized network; and optimizing the initialized network based on the CSO algorithm and the decision variable, to obtain the optimized network.

Preferably, the establishing an input weight matrix of the initialized network by the matrix generation method of singular value decomposition includes:

establishing a first singular value;

establishing a first diagonal matrix based on the first singular value;

establishing a random matrix based on the first diagonal matrix;

generating two orthogonal matrixes based on the random matrix; and obtaining the input weight matrix of the initialized network based on the two orthogonal matrixes.

Preferably, the establishing a reservoir weight of the initialized network by the matrix generation method of singular value decomposition includes:

establishing a second singular value;

establishing a second diagonal matrix based on the second singular value;

randomly generating two rotation matrixes based on the second diagonal matrix; and establishing the reservoir weight of the initialized network based on the two rotation matrixes.

Preferably, the optimizing the initialized network based on the CSO algorithm and the decision variable, to obtain the optimized network includes:

dividing the decision variable into a structure-related hyper-parameter and a weight-related variable;

optimizing the structure-related hyper-parameter and a randomly generated weight variable by using a prediction accuracy as an objective function and based on the CSO algorithm, to obtain a first optimal parameter;

optimizing the weight-related variable and the first optimal parameter by using the prediction accuracy as the objective function and based on the CSO algorithm, to obtain a second optimal parameter optimizing a parameter of the initialized network based on the first optimal parameter and the second optimal parameter, to obtain the optimized network.

A system for predicting effluent $NH_4$—N includes:

a data obtaining module, configured to obtain data to be tested; and a concentration prediction module, configured to input the data to be tested into a trained deep echo state network, to obtain predicted $NH_4$—N concentration, where the deep echo state network includes:

an original network establishing module, configured to establish an original network, where the original network includes a plurality of input variables and reservoirs, and a principal component analysis (PCA) mapping layer is added between adjacent ones of the reservoirs;

an original network initialization module, configured to initialize the original network to obtain an initialized network;

a network optimization module, configured to perform parameter optimization on the initialized network by a matrix generation method of singular value decomposition and a competitive swarm optimizer (CSO) algorithm, to obtain an optimized network; and a network test module, configured to train and test the optimized network, to obtain the trained deep echo state network.

Preferably, the original network initialization module includes:

an original network parameter setting unit and an original network structure setting unit.

Preferably, the network optimization module includes:

an input variable establishing unit, configured to establish an input weight matrix and a reservoir weight of the initialized network by the matrix generation method of singular value decomposition;

a decision variable determination unit, configured to determine a decision variable based on the input weight matrix, the reservoir weight, and a delay factor of the initialized network; and a network optimization module, configured to optimize the initialized network based on the CSO algorithm and the decision variable, to obtain the optimized network.

The present disclosure further provides an electronic device, including:

one or more processors; and a storage apparatus, configured to store one or more programs;

when the one or more programs are executed, the one or more processors are enabled to implement the method for predicting effluent $NH_4$—N according to any one of claims 1 to 9.

The storage apparatus is a readable storage medium.

According to specific embodiments provided by the present disclosure, the present disclosure provides the following technical effects:

According the method and system for predicting effluent $NH_4$—N and the electronic device provided by the present disclosure, the deep echo state network is established by adding the PCA mapping layer and the delay factor into the network, the parameters in the network are optimized by a singular value decomposition based matrices design strategy-competitive swarm optimizer (SVDMDS-CSO) algorithm to obtain the trained deep echo state network, and a concentration of ammonia nitrogen in a sewage treatment process is predicted through the network, so that accuracy and stability of prediction are improved, and an error of a prediction result and maintenance costs are reduced.

BRIEF DESCRIPTION OF THE DRAWINGS

To describe the technical solutions in embodiments of the present disclosure or in the prior art more clearly, the accompanying drawings required in embodiments are briefly described below. Apparently, the accompanying drawings in the following description show only some embodiments of the present disclosure, and other drawings can be derived from these accompanying drawings by those of ordinary skill in the art without creative efforts.

DETAILED DESCRIPTION OF THE EMBODIMENTS

To technical solutions of embodiments of the present disclosure are clearly and completely described below with reference to the drawings. Apparently, the described embodiments are only a part rather than all of embodiments of the present disclosure. All other embodiments obtained by a person of ordinary skill in the art based on embodiments of the present disclosure without creative efforts shall fall within the protection scope of the present disclosure.

The "embodiment" mentioned herein means that a specific feature, structure or characteristic described in combination with embodiment may be included in at least one embodiment of the present application. The term appearing in different parts of the specification does not necessarily refer to the same embodiment or an independent or alternative embodiment exclusive of other embodiments. It may be explicitly or implicitly appreciated by those skilled in the art that the embodiment described herein may be combined with other embodiments.

The terms "first", "second", "third", "fourth", and the like in the specification, claims and the accompanying drawings of the present disclosure are intended to distinguish between different objects but do not indicate a specific sequence. Moreover, the terms "include", "have", and any variations thereof mean to cover non-exclusive inclusion. For example, a process or method that includes a series of steps or units is not limited to the listed steps. On the contrary, optionally, it also includes steps that are not listed, or optionally also includes other steps inherent to the process, method, product, or device.

An objective of the present disclosure is to provide a method for predicting effluent ammonia nitrogen ($NH_4$—N), to resolve problems of predicting the effluent $NH_4$—N in a conventional technology, for example, low prediction accuracy, weak stability, and high maintenance cost.

To make the above objectives, features, and advantages of the present disclosure clearer and more comprehensible, the present disclosure will be further described in detail below with reference to the accompanying drawings and the specific examples.

Embodiment 1

Figures 1, 2:
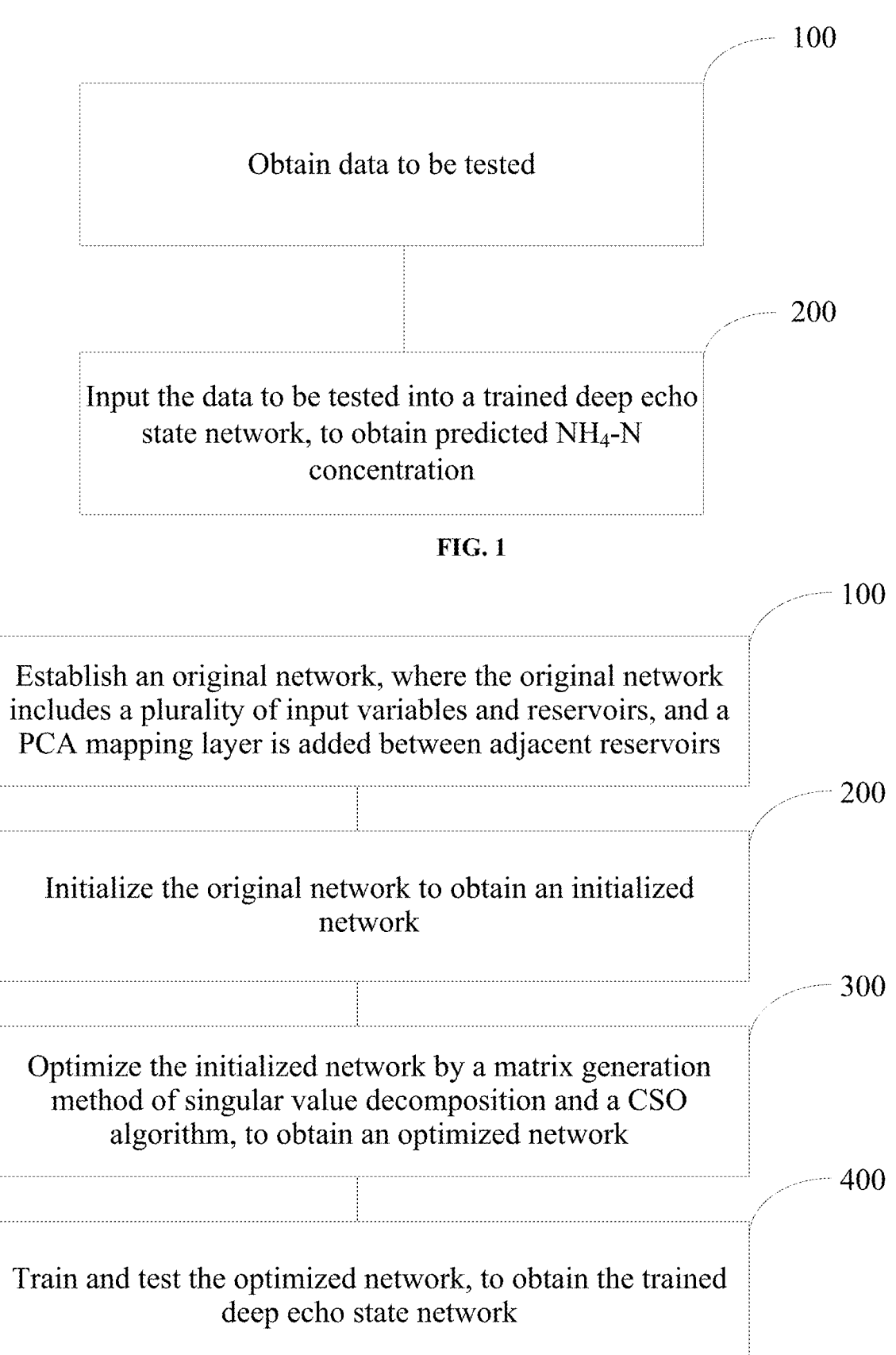
FIG. 1 is a schematic flowchart of a method for predicting effluent $NH_4$—N according to an embodiment of the present disclosure.
FIG. 2 is a flowchart of a method for establishing a deep echo state network according to an embodiment of the present disclosure.

Referring to FIG. 1, the present disclosure provides a method for predicting effluent ammonia nitrogen ($NH_4$—N). The method includes the following steps.

Step 100: Obtain data to be tested.

Step 200: Input the data to be tested into a trained deep echo state network, to obtain predicted $NH_4$—N concentration.

As shown in FIG. 2, a method for establishing the deep echo state network includes the following steps.

Step 201: Establish an original network, where the original network includes a plurality of input variables and reservoirs, and a principal component analysis (PCA) mapping layer is added between adjacent ones of the reservoirs.

Step 202: Initialize the original network to obtain an initialized network.

Step 203: Perform parameter optimization on the initialized network by a matrix generation method of singular value decomposition and a competitive swarm optimizer (CSO) algorithm, to obtain an optimized network.

Step 204: Train and test the optimized network, to obtain the trained deep echo state network.

Further, the input variable includes:

a temperature, a redox potential, a dissolved oxygen concentration, content of total suspended solids, a pH value, total effluent phosphorus, and total influent phosphorus.

Figure 3:
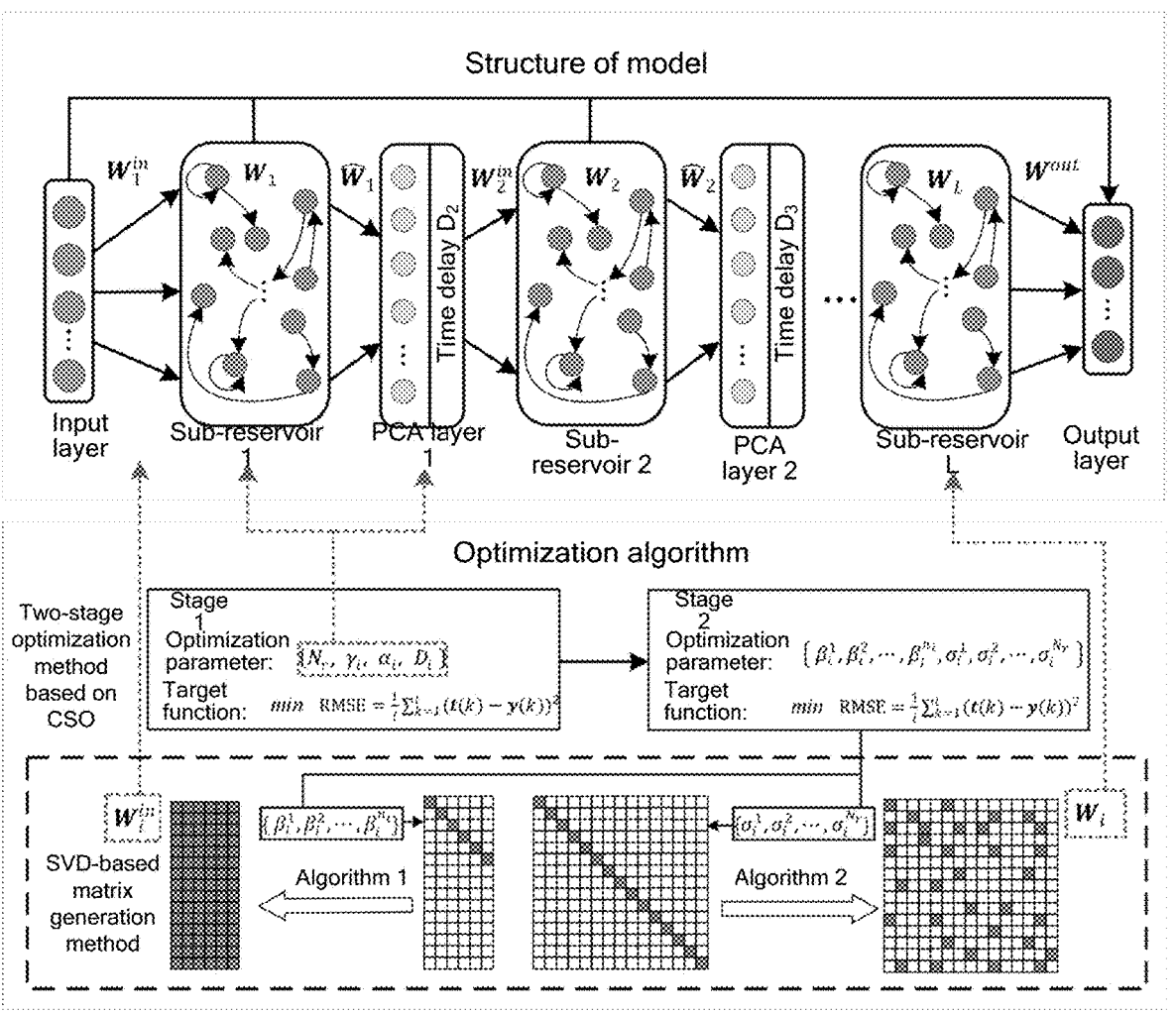
FIG. 3 is a diagram of a structure of an Evolving Deep Delay Echo State Network (EDDESN) according to an embodiment of the present disclosure.
Figure 4:
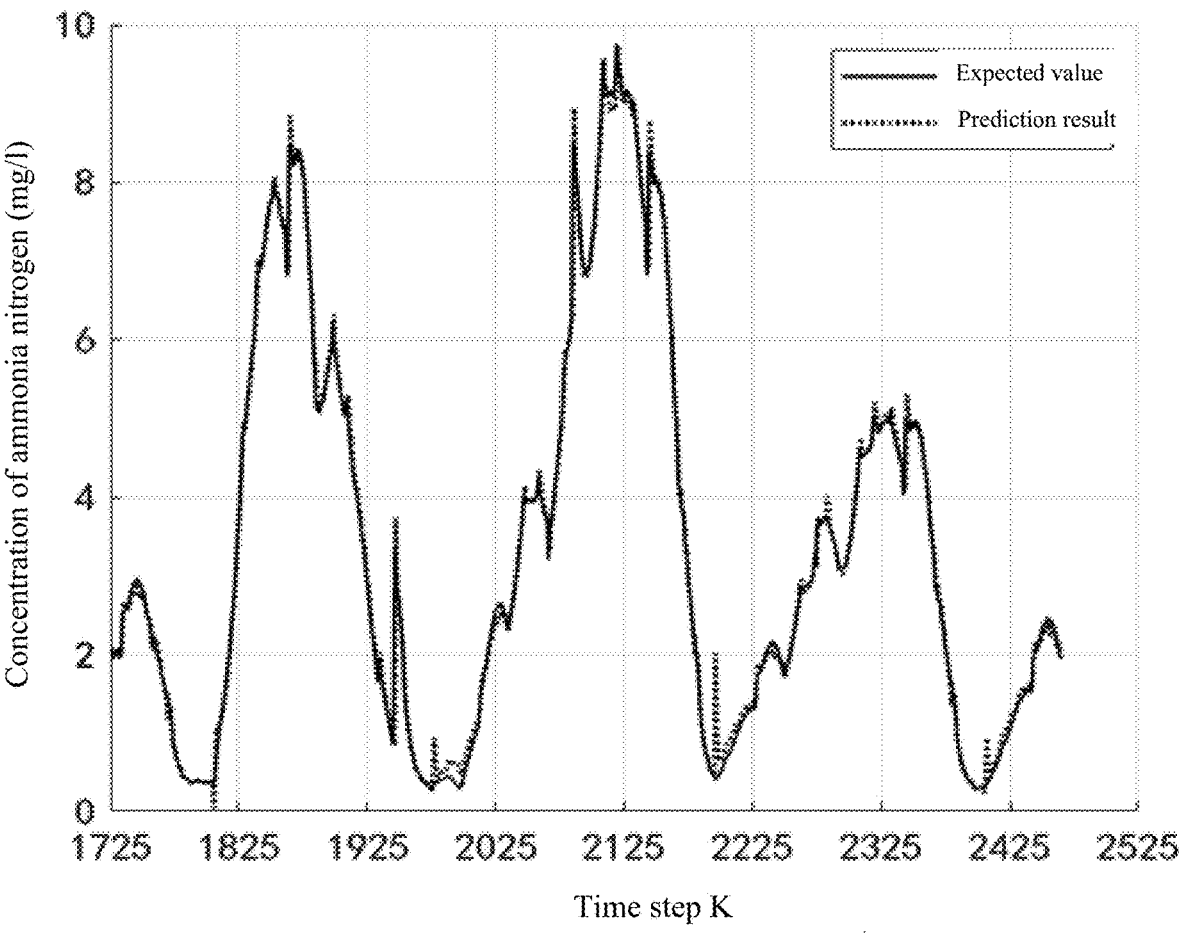
FIG. 4 is a diagram of a prediction result of a concentration of effluent $NH_4$—N according to an embodiment of the present disclosure.
Figure 5:
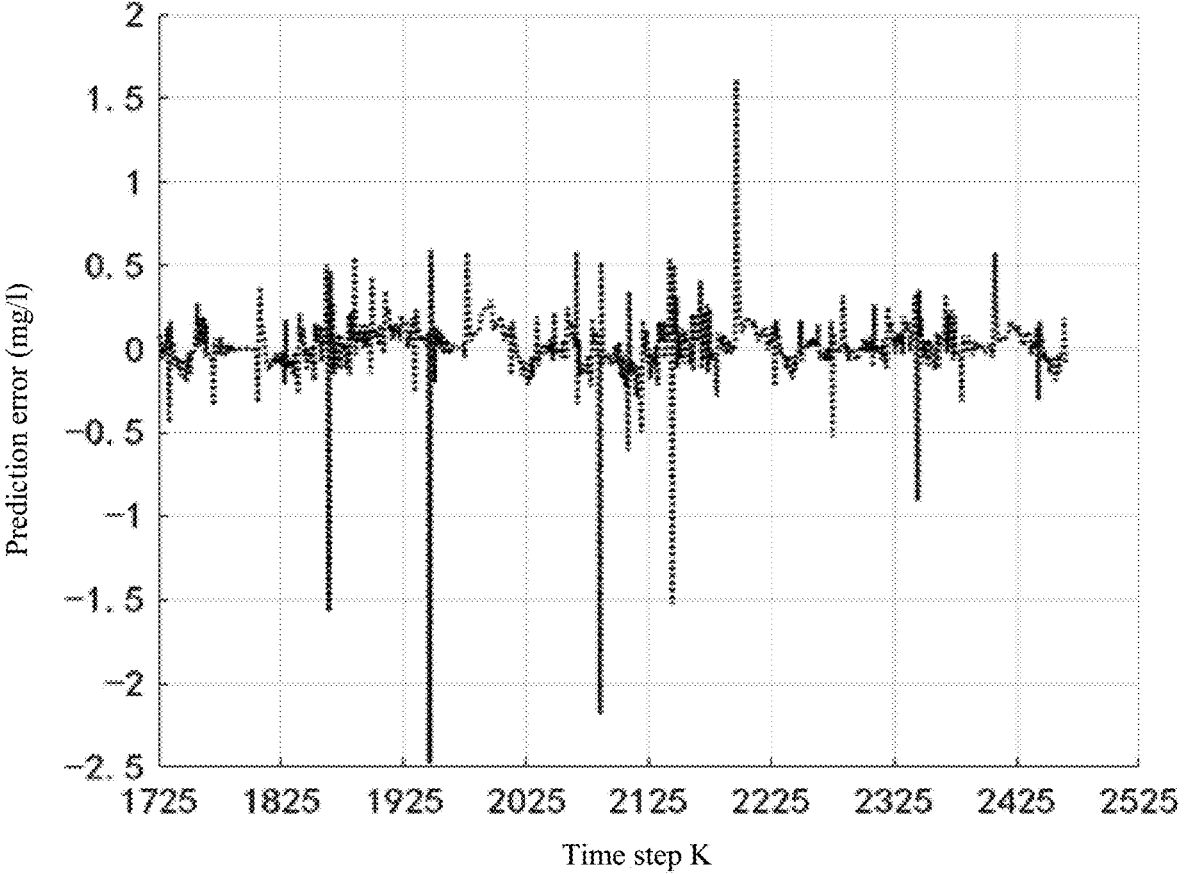
FIG. 5 is a diagram of a prediction error of a concentration effluent $NH_4$—N according to an embodiment of the present disclosure.

Further, as shown in FIG. 3 to FIG. 5, the initializing the original network includes:

setting a parameter of the original network and setting a structure of the original network.

Specifically, the setting a structure of the original network includes:

converting all the input variables into five input nodes by a principal component analysis method; and determining the structure of the original network based on the input nodes and effluent $NH_4$—N concentration. The network structure is 5-1, where L represents a quantity of layers of the network and $N_r$ represents a quantity of nodes in the reservoir. In this network, L=3, $N_r \in [100, 200]$. That is, the network has: five input nodes; three sub-reservoirs, where a quantity of neurons in each reservoir is limited within a range of [100, 200], and further determined by the optimization algorithm; and one output node. A PCA layer between adjacent sub-reservoirs has 60 nodes, to reduce dimension of an input weight.

Specifically, the setting a parameter of the original network includes:

using a tan h function as an activation function of a neuron, and initializing the parameter of the original network. The reservoir uses a leaky neuron and uses the tan h function as the activation function of the neuron to train a sample $\{(u_k, t_k \in | u_k \in R^n, k=1, 2, \ldots, 1\}$, where $u_k$ represents a $k^{th}$ group of input samples, $t_k$ indicates kth group of actual output values, n represents dimension of an input sample, and 1 represents a total quantity of samples. Other related parameters are obtained by a subsequent optimization algorithm.

Further, the performing parameter optimization on the initialized network by a matrix generation method of singular value decomposition and a competitive swarm optimizer (CSO) algorithm, to obtain an optimized network includes:

establishing an input weight matrix and a reservoir weight of the initialized network by the matrix generation method of singular value decomposition;

determining a decision variable based on the input weight matrix, the reservoir weight, and a delay factor of the initialized network; and optimizing the initialized network based on the CSO algorithm and the decision variable, to obtain the optimized network.

Specifically, the establishing an input weight matrix of the initialized network by the matrix generation method of singular value decomposition includes the following steps.

Establish a first singular value. First, a group of singular values $$\{\beta_i^1, \beta_i^2, \ldots, \beta_i^{n_i}\}$$

are set, where i represents an $i^{th}$ reservoir, and $n_i$ represents input dimension of an $i^{th}$ sub-reservoir.

Establish a first diagonal matrix $$S = \text{diag}(\beta_i^1, \beta_i^2, \ldots, \beta_i^{n_i})$$

based on the first singular value, where $$\beta_i^1 \geq \beta_i^2 \geq \ldots \geq \beta_i^{n_i}.$$

Establish a random matrix $$\sum_i^{in} = [S; 0] \in R^{N_i \times n_i}$$

based on the first diagonal matrix.

Generate two orthogonal matrixes $U \in R^{N_r \times N_r}$ and $V \in R^{n_i \times n_i}$ based on the random matrix.

Obtain an $i^{th}$ input weight matrix $$W_i^{in} = U \sum_i^{in} V$$

of the initialized network based on the two orthogonal matrixes.

Specifically, the establishing a reservoir weight of the initialized network by the matrix generation method of singular value decomposition includes the following steps.

Establish a second singular value $$\{\sigma_i^1, \sigma_i^2, \ldots, \sigma_i^{N_r}\}.$$

Establish a second diagonal matrix $$\sum\nolimits_i = \mathrm{diag}\left(\sigma_i^1, \sigma_i^2, \ldots, \sigma_i^{N_r}\right)$$

based on the second singular value, where $$\sigma_i^1 \geq \sigma_i^2 \geq \ldots \geq \sigma_i^{N_r}.$$

Randomly generate two rotation matrixes $U=Q (p_1, q_1, s_1)$ and $V=Q(p_2, q_2, s_2)$ based on the second diagonal matrix, where $Q(p,q,s)$ represents $Q_{p,p}=Q_{q,q}=\cos(s)$, $Q_{p,q}=-\sin(s)$, and $Q_{q,p}=\sin(s)$, p and q are two integers in $[1,N_r]$ and s is a rotation angle in $[0,2\pi]$.

Establish the reservoir weight $W_i=U\Sigma_i V$ of the initialized network based on the two rotation matrixes, and repeat the foregoing steps until sparsity of the matrix meets requirements.

Specifically, the optimizing the initialized network based on the CSO algorithm and the decision variable, to obtain the optimized network includes the following steps.

Determine the decision variable as $$\{N_r, \gamma_i, \alpha_i, D_i, \sigma_i^1, \sigma_i^2, \ldots, \sigma_i^{N_r}, \beta_i^1, \beta_i^2, \ldots, \beta_i^{n_i} | i = 1, 2, \ldots, L\},$$

where
$N_r$ represents a size of the sub-reservoir, $\gamma_i$ represents a leak rate of neurons in the $i^{th}$ sub-reservoir, $\alpha_i$ represents sparsity of the reservoir weight matrix, and $D_i$ represents a delay size of the delay factor.

To reduce dimension of the decision variable, divide the decision variable into a structure-related hyper-parameter and a weight-related variable, namely $\{N_r, \gamma_i, \alpha_i D_i | i=1, 2, \ldots, L\}$ and $$\{\sigma_i^1, \sigma_i^2, \ldots, \sigma_i^{N_r}, \beta_i^1, \beta_i^2, \ldots, \beta_i^{n_i} | i = 1, 2, \ldots, L\}.$$

In a first stage, if the decision variable is $\{N_r, \gamma_i, \alpha_i D_i | i=1, 2, \ldots, L\}$, optimize the structure-related hyper-parameter and a randomly generated weight variable by using a prediction accuracy as an objective function and based on the CSO algorithm, to obtain a first optimal parameter.

In a second stage, if the decision variable is $$\{\sigma_i^1, \sigma_i^2, \ldots, \sigma_i^{N_r}, \beta_i^1, \beta_i^2, \ldots, \beta_i^{n_i} | i = 1, 2, \ldots, L\},$$

optimize the weight-related variable and the first optimal parameter by using the prediction accuracy as the objective function and based on the CSO algorithm, to obtain a second optimal parameter. The algorithm is suitable for a high-dimensional optimization problem.

Optimize a parameter of the initialized network based on the first optimal parameter and the second optimal parameter, to obtain the optimized network.

A state equation of the above-mentioned network of which initialization and parameter optimization are completed is:

$$x_i(k) = (1 - \gamma_i)x_i(k - 1) + \gamma_i f\left[W_i^{in} u_i(k) + W_i x_i(k - 1)\right],$$

where
$x_i(k)$ represents a state of an $i^{th}$ sub-reservoir at $k^{th}$ time, $\gamma_i$ represents the leak rate of the neurons in the $i^{th}$ sub-reservoir, f represents the activation function tan h, $$W_i^{in}$$

represents the input weight of the $i^{th}$ sub-reservoir, and $W_i$ represents an internal weight of the $i^{th}$ sub-reservoir. $u_i(k)$ represents an input of the $i^{th}$ sub-reservoir, and may be expressed as:

$$u_i(k) = \begin{cases} u(k), i = 1 \\ \hat{W}_{i-1} x_{i-1}(k - D_i), 1 < i \leq L \end{cases},$$

where
$D_i$ represents a size of an $i^{th}$ delay factor, $\hat{W}_i$ represents a linear transformation matrix calculated by PCA. To calculate the matrix, first, calculate an average value of a state vector $x_i=[x_{i1}, x_{i2}, \ldots x_{iN_r}]$, where $X_i$ represents the state vector.

$$\mu_i = \frac{1}{N_r} \sum_{j=1}^{N_r} x_{ij},$$

where ui represents the average value of the state vector.

Decentralize the state vector to obtain $Z_i=[x_{i1}-\mu_i, x_{i2}-\mu_i, \ldots, x_{iN}-\mu_i]$, where Zi represents a decentralized state vector.

Calculate a covariance matrix:

$$S_i = \frac{1}{l-1} Z_i Z_i^T,$$

where Si represents the covariance matrix.

$\hat{W}_i$ is formed with feature vectors corresponding to first M maximum eigenvalues of $S_i$.

An output of the optimized network may be expressed as $y(k)=X(k)W^{out}$, where y(k) represents the output of the optimized network.

$X(t)=[x_1(t); x_2(t); \ldots; x_L(t)]^T$ represents a state matrix. To avoid ill-posed issue and collinearity problem, calculate the output weight by ridge regression:

$$W^{out} = \arg \min_{W^{out}} \|HW^{out} - T\|_2^2 + \beta \|W^{out}\|_2^2,$$

where $H=[X(1), X(2), \ldots, X(l)]^T$ represents the state matrix, and $T=[t(1), t(2), \ldots, t(l)]^T$ represents an expected output vector. $W^{out}=(H^TH+\beta I)^{-1}H^TT$ is obtained by a least square method.

Input a test sample to test the optimized network based on the output weight $W^{out}$ obtained in the foregoing step, to obtain the trained deep echo state network.

Embodiment 2

A system for predicting effluent ammonia nitrogen ($NH_4$—N) includes a data obtaining module and a concentration prediction module.

The data obtaining module is configured to obtain data to be tested.

The concentration prediction module is configured to input the data to be tested into a trained deep echo state network, to obtain predicted $NH_4$—N concentration.

The deep echo state network includes an original network establishing module, an original network initialization module, a network optimization module, and a network test module.

The original network establishing module is configured to establish an original network, where the original network includes a plurality of input variables and reservoirs, and a principal component analysis (PCA) mapping layer is added between adjacent ones of the reservoirs, and the input variable includes a temperature, a redox potential, a dissolved oxygen concentration, content of total suspended solids, a pH value, total effluent phosphorus, and total influent phosphorus.

The original network initialization module is configured to initialize the original network to obtain an initialized network. The original network initialization module includes an original network parameter setting unit and an original network structure setting unit.

The original network structure setting unit includes a variable conversion subunit, configured to convert all the input variables into five input nodes by a principal component analysis method; an original network structure determining subunit, configured to determine a structure of the original network based on an input node and a concentration of the effluent $NH_4$—N.

The original network parameter setting unit uses a tan h function as an activation function of a neuron, and initializes the parameter of the original network.

The network optimization module is configured to perform parameter optimization on the initialized network by a matrix generation method of singular value decomposition and a competitive swarm optimizer (CSO) algorithm, to obtain an optimized network.

Specifically, the network optimization module includes an input variable establishing unit, configured to establish an input weight matrix and a reservoir weight of the initialized network by the matrix generation method of singular value decomposition; and a decision variable determination unit, configured to determine a decision variable based on the input weight matrix, the reservoir weight, and a delay factor of the initialized network; and a decision variable determination unit, configured to optimize the initialized network based on the CSO algorithm and the decision variable, to obtain the optimized network.

In the input variable establishing unit, the method for establishing an input weight matrix specifically includes: establishing a first diagonal matrix based on the first singular value; establishing a first diagonal matrix based on the first singular value; establishing a random matrix based on the first diagonal matrix; generating two orthogonal matrixes based on the random matrix; and obtaining the input weight matrix of the initialized network based on the two orthogonal matrixes.

In the input variable establishing subunit, the method for establishing a reservoir weight matrix specifically includes: establishing a second singular value; establishing a second singular value; randomly generating two rotation matrixes based on the second diagonal matrix; and establishing the reservoir weight of the initialized network based on the two rotation matrixes.

The network optimization unit is specifically configured to: divide the decision variable into a structure-related hyper-parameter and a weight-related variable; optimize based on the structure-related hyper-parameter and a randomly generated weight variable by using a prediction accuracy as an objective function based on the CSO algorithm, to obtain a first optimal parameter; optimize the weight-related variable and the first optimal parameter by using the prediction accuracy as the objective function and based on the CSO algorithm, to obtain a second optimal parameter; and optimize the parameter of the initialized network based on the first optimal parameter and the second optimal parameter, to obtain the optimized network.

The network test module is configured to train and test the optimized network, to obtain the trained deep echo state network.

Embodiment 3

An electronic device includes:

one or more processors and a storage apparatus.

The storage apparatus is configured to store one or more programs.

When the one or more programs are executed, the one or more processors are enabled to implement the method for predicting effluent $NH_4$—N in the embodiment 1.

The storage apparatus is a readable storage medium.

The present disclosure has the following beneficial effects:

According to the method and system for predicting effluent ammonia nitrogen ($NH_4$—N) and the electronic device provided by the present disclosure, the deep echo state network is established by adding the PCA mapping layer and the delay factor into the network, the parameters in the network are optimized by a singular value decomposition based matrices design strategy-competitive swarm optimizer (SVDMDS-CSO) algorithm to obtain the trained deep echo state network, and a concentration of ammonia nitrogen in a sewage treatment process is predicted through the network, so that accuracy and stability of prediction are improved, and an error of a prediction result and maintenance costs are reduced.

Each embodiment of the present specification is described in a progressive manner, each embodiment focuses on the difference from other embodiments, and the same and similar parts between embodiments may refer to each other. Since the system disclosed in an embodiment corresponds to the method disclosed in another embodiment, the description is relatively simple, and reference can be made to the method description.

Methods described herein may be construed as being performed or performable by a module, segment or portion of code representing executable instructions including one or more steps for implementing a particular logical function or process. The steps do not necessarily need to be performed in the order shown or discussed herein, and in at least some cases could be performed in a substantially concurrent manner or in a different order.

The methods described herein may be considered as including executable instructions for implementing logical steps or functions. They can be specifically embodied in any computer-readable medium for use by an apparatus or device for executing instructions, such as a computer-based system, a system including a processor, or another system that can obtain instructions from the apparatus or device and execute these instructions, or for use in conjunction with the apparatus or device. For the purposes of the present specification, "computer-readable medium" can be any means that can contain, store, communicate, propagate or transmit programs for use by an apparatus or device for executing instructions, or for use in conjunction with the apparatus or device for executing instructions.

The computer-readable medium referred to herein may take any form, such as a magnetic or optical disc drive, a random access memory (RAM), a read only memory (ROM), an erasable programmable read-only memory (EPROM or flash memory), or others.

The elements of electronic devices in the present disclosure that are referred to as "modules" or "units" (or other terms) may be implemented in the form of hardware, software, firmware, or a combination thereof. In at least some disclosed embodiments, modules that are configured to perform certain steps or methods may be implemented using firmware or software stored in a memory and executed by a suitable instruction execution system, such as a computer including a processor, for example. Modules implemented in hardware in some embodiments may take the form of discrete logic circuits for implementing logic functions, application-specific integrated circuits having suitable combined logic gate circuits, programmable gate arrays (PGA), field programmable gate arrays (FPGA), or others.

Specific examples are used herein to explain the principles and implementations of the present disclosure. The foregoing description of embodiments is only intended to help understand the method of the present disclosure and its core ideas; besides, various modifications may be made by a person of ordinary skill in the art to specific embodiments and the scope of application in accordance with the ideas of the present disclosure. In conclusion, the content of the present specification shall not be construed as limitations to the present disclosure.

What is claimed is:

1. A method for predicting effluent ammonia nitrogen (NH$_4$—N), comprising:
   obtaining data to be tested; and
   inputting the data to be tested into a trained deep echo state network, to obtain predicted NH$_4$—N concentration,
   wherein a method for establishing the deep echo state network comprises:
      establishing an original network, wherein the original network comprises a plurality of input variables and reservoirs, and a principal component analysis (PCA) mapping layer is added between adjacent ones of the reservoirs;
      initializing the original network to obtain an initialized network;
      performing parameter optimization on the initialized network by a matrix generation method of singular value decomposition and a competitive swarm optimizer (CSO) algorithm, to obtain an optimized network; and training and testing the optimized network, to obtain the trained deep echo state network.

2. The method for predicting effluent NH$_4$—N according to claim 1, wherein the input variables comprise:
   a temperature, a redox potential, a dissolved oxygen concentration, content of total suspended solids, a pH value, total effluent phosphorus, and total influent phosphorus.

3. The method for predicting effluent NH$_4$—N according to claim 2, wherein the initializing the original network comprises:
   setting a parameter of the original network and setting a structure of the original network.

4. The method for predicting effluent NH$_4$—N according to claim 3, wherein the setting a structure of the original network comprises:
   converting all the input variables into five input nodes by a principal component analysis method; and
   determining the structure of the original network based on the input nodes and effluent NH$_4$—N concentration.

5. The method for predicting effluent NH$_4$—N according to claim 3, wherein the setting a parameter of the original network comprises:
   using a tan h function as an activation function of a neuron, and initializing the parameter of the original network.

6. The method for predicting effluent NH$_4$—N according to claim 1, wherein the performing parameter optimization on the initialized network by a matrix generation method of singular value decomposition and a competitive swarm optimizer (CSO) algorithm, to obtain an optimized network comprises:
   establishing an input weight matrix and a reservoir weight of the initialized network by the matrix generation method of singular value decomposition;
   determining a decision variable based on the input weight matrix, the reservoir weight, and a delay factor of the initialized network; and
   optimizing the initialized network based on the CSO algorithm and the decision variable, to obtain the optimized network.

7. The method for predicting effluent NH$_4$—N according to claim 6, wherein the establishing an input weight matrix of the initialized network by the matrix generation method of singular value decomposition comprises:
   establishing a first singular value;
   establishing a first diagonal matrix based on the first singular value;
   establishing a random matrix based on the first diagonal matrix;
   generating two orthogonal matrixes based on the random matrix; and
   obtaining the input weight matrix of the initialized network based on the two orthogonal matrixes.

8. The method for predicting effluent NH$_4$—N according to claim 6, wherein the establishing a reservoir weight of the initialized network by the matrix generation method of singular value decomposition comprises:
   establishing a second singular value;
   establishing a second diagonal matrix based on the second singular value;
   randomly generating two rotation matrixes based on the second diagonal matrix; and
   establishing the reservoir weight of the initialized network based on the two rotation matrixes.

9. The method for predicting effluent NH$_4$—N according to claim 6, wherein the optimizing the initialized network based on the CSO algorithm and the decision variable, to obtain the optimized network comprises:

dividing the decision variable into a structure-related hyper-parameter and a weight-related variable;

optimizing the structure-related hyper-parameter and a randomly generated weight variable by using a prediction accuracy as an objective function and based on the CSO algorithm, to obtain a first optimal parameter;

optimizing the weight-related variable and the first optimal parameter by using the prediction accuracy as the objective function and based on the CSO algorithm, to obtain a second optimal parameter; and optimizing a parameter of the initialized network based on the first optimal parameter and the second optimal parameter, to obtain the optimized network.

10. An electronic device, comprising:

one or more processors; and a storage apparatus, configured to store one or more programs, wherein when the one or more programs are executed, the one or more processors are enabled to implement the method for predicting effluent $NH_4$—N according to claim 1.

11. The electronic device according to claim 10, wherein the input variables comprise:

a temperature, a redox potential, a dissolved oxygen concentration, content of total suspended solids, a pH value, total effluent phosphorus, and total influent phosphorus.

12. The electronic device according to claim 11, wherein the initializing the original network comprises:

setting a parameter of the original network and setting a structure of the original network.

13. The electronic device according to claim 12, wherein the setting a structure of the original network comprises:

converting all the input variables into five input nodes by a principal component analysis method; and determining the structure of the original network based on the input nodes and effluent $NH_4$—N concentration.

14. The electronic device according to claim 12, wherein the setting a parameter of the original network comprises:

using a tan h function as an activation function of a neuron, and initializing the parameter of the original network.

15. The electronic device according to claim 13, wherein the performing parameter optimization on the initialized network by a matrix generation method of singular value decomposition and a competitive swarm optimizer (CSO) algorithm, to obtain an optimized network comprises:

establishing an input weight matrix and a reservoir weight of the initialized network by the matrix generation method of singular value decomposition;

determining a decision variable based on the input weight matrix, the reservoir weight, and a delay factor of the initialized network; and optimizing the initialized network based on the CSO algorithm and the decision variable, to obtain the optimized network.

16. The electronic device according to claim 15, wherein the establishing an input weight matrix of the initialized network by the matrix generation method of singular value decomposition comprises:

establishing a first singular value;

establishing a first diagonal matrix based on the first singular value;

establishing a random matrix based on the first diagonal matrix;

generating two orthogonal matrixes based on the random matrix; and obtaining the input weight matrix of the initialized network based on the two orthogonal matrixes.

17. The electronic device according to claim 10, wherein the storage apparatus is a readable storage medium.

18. A system for predicting effluent $NH_4$—N, comprising:

a data obtaining module, configured to obtain data to be tested; and a concentration prediction module, configured to input the data to be tested into a trained deep echo state network, to obtain predicted $NH_4$—N concentration, wherein the deep echo state network comprises:

an original network establishing module, configured to establish an original network, wherein the original network comprises a plurality of input variables and reservoirs, and a principal component analysis (PCA) mapping layer is added between adjacent ones of the reservoirs;

an original network initialization module, configured to initialize the original network to obtain an initialized network;

a network optimization module, configured to perform parameter optimization on the initialized network by a matrix generation method of singular value decomposition and a competitive swarm optimizer (CSO) algorithm, to obtain an optimized network; and a network test module, configured to train and test the optimized network, to obtain the trained deep echo state network.

19. The system for predicting effluent $NH_4$—N according to claim 18, wherein the original network initialization module comprises:

an original network parameter setting unit and an original network structure setting unit.

20. The system for predicting effluent $NH_4$—N according to claim 18, wherein the network optimization module comprises:

an input variable establishing unit, configured to establish an input weight matrix and a reservoir weight of the initialized network by the matrix generation method of singular value decomposition;

a decision variable determination unit, configured to determine a decision variable based on the input weight matrix, the reservoir weight, and a delay factor of the initialized network; and a network optimization module, configured to optimize the initialized network based on the CSO algorithm and the decision variable, to obtain the optimized network.

* * * * *